(12) United States Patent
Marini

(10) Patent No.: US 7,879,910 B1
(45) Date of Patent: Feb. 1, 2011

(54) COMPOSITIONS AND METHODS FOR PROMOTING LUSH HAIR GROWTH

(75) Inventor: Jan Marini, San Jose, CA (US)

(73) Assignee: Jan Marini Skin Research, Inc., San Jose, CA (US)

( * ) Notice: Subject to any disclaimer, the term of this patent is extended or adjusted under 35 U.S.C. 154(b) by 589 days.

(21) Appl. No.: 11/973,959

(22) Filed: Oct. 10, 2007

Related U.S. Application Data

(60) Provisional application No. 60/850,434, filed on Oct. 10, 2006, provisional application No. 60/874,981, filed on Dec. 15, 2006, provisional application No. 60/924,721, filed on May 29, 2007.

(51) Int. Cl.
*A61K 8/00* (2006.01)
*A61K 8/18* (2006.01)
*A61K 31/19* (2006.01)

(52) U.S. Cl. .................... 514/573; 424/49; 424/63; 424/70.1

(58) Field of Classification Search .................. 424/49, 424/63, 70.1; 514/573
See application file for complete search history.

(56) References Cited

U.S. PATENT DOCUMENTS

| | | | |
|---|---|---|---|
| 2,798,053 A | 7/1957 | Brown | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,087,445 A | 2/1992 | Haffey et al. | |
| 5,100,660 A | 3/1992 | Hawe et al. | |
| 6,262,105 B1 | 7/2001 | Johnstone | |
| 6,492,326 B1 | 12/2002 | Robinson et al. | |
| 6,896,877 B2 | 5/2005 | Calello et al. | |
| 6,974,799 B2 | 12/2005 | Lintner | |
| 7,070,768 B2 * | 7/2006 | Krauss | 424/59 |
| 7,351,404 B2 | 4/2008 | Woodward et al. | |
| 7,388,029 B2 | 6/2008 | Delong et al. | |
| 2003/0147823 A1 | 8/2003 | Woodward et al. | |
| 2004/0052760 A1 | 3/2004 | Michelet et al. | |
| 2004/0225014 A1 | 11/2004 | Habe et al. | |
| 2004/0242665 A1 | 12/2004 | Boulle et al. | |
| 2005/0042191 A1 | 2/2005 | Travkina et al. | |

FOREIGN PATENT DOCUMENTS

| | | |
|---|---|---|
| EP | 0228868 A2 | 7/1987 |
| EP | 0228868 A3 | 1/1988 |

OTHER PUBLICATIONS

Nikitakis, et al. CTFA International Cosmetic Ingredient Dictionary, Fourth Edition. Cosmetic, Toiletry, and Fragrance Association. 1991; pp. 12, 80.

Urtti, et al. Minimizing systemic absorption of topically administered ophthalmic drugs. Surv Ophthalmol. May-Jun. 1993;37(6):435-56.

Wenninger, et al. International Cosmetic Ingredient Dictionary and Handbook, 10th Edition. Cosmetic, Toiletry, and Fragrance Association. 2003; 2217-2227.

* cited by examiner

*Primary Examiner*—Raymond J Henley, III
(74) *Attorney, Agent, or Firm*—Wilson, Sonsini Goodrich & Rosati

(57) ABSTRACT

Compositions, kits and methods are provided for conditioning, revitalizing, volumizing or increasing the natural pigmentation of the hair, including hair on the scalp, eyelashes, eyebrows, mustache and beard, promoting healthy growth, and treating and preventing loss, thinning or miniaturization of hair due to aging, various genetic, pathological, radiation, chemotherapy, chemical treatment environmental or other reasons.

59 Claims, 20 Drawing Sheets

COMPOSITIONS AND METHODS FOR PROMOTING LUSH HAIR GROWTH

CROSS-REFERENCE

This application claims the benefit of U.S. Provisional Application No. 60/850,434, filed Oct. 10, 2006; U.S. Provisional Application No. 60/874,981, filed Dec. 15, 2006; and U.S. Provisional Application No. 60/924,721, filed May 29, 2007, which applications are incorporated herein by reference in their entirety.

BACKGROUND OF THE INVENTION

As we age, so too does our hair. Aging hair appears to have less body, bounce and vitality; it becomes sparse and thin. This is exacerbated by exposure to environmental stressors and pollutants, including ultraviolet radiation, and to chemicals in hair treatments. The pursuit of lusher, fuller, longer, and thicker hair including hair on the scalp, eyelashes, eyebrows, mustache and beard has given rise to a multitude of ingredient technologies and treatments, offered through a variety of retail channels and by professional providers. In particular, appearance-enhancing regimens have long included application of cosmetic products applied to the area around the eyes, such as by using false eyelashes and hair extension using synthetic or human hair grafting. False eyelashes and hair grafts, however, can be difficult to use and hard to remove, frequent use of which may result in damages and loss of hair. Mascaras and hair thickening gels have well-known drawbacks; often, a waxy-build up causes hair to become brittle and break.

There has been, and remains, a need for products and treatment regimen that creates the appearance of thicker, more voluminous hair while at the same time improving the condition of hair—making them suppler, lusher, less brittle and less susceptible to breakage. This need is met by compositions and methods of the present invention.

SUMMARY OF THE INVENTION

The present invention provides innovative compositions, kits and methods for conditioning and volumizing the hair, including but are not limited to hair on the scalp, eyelashes, eyebrows, mustache and beard, promoting healthy growth and treating and preventing loss or thinning of hair due to aging, various genetic, pathological, radiation, chemotherapy, chemical treatment environmental, and other reasons.

In one aspect, a composition is provided, which can be useful for promoting hair growth, conditioning or preventing hair loss. The composition comprises a compound of Formula I having the structure of

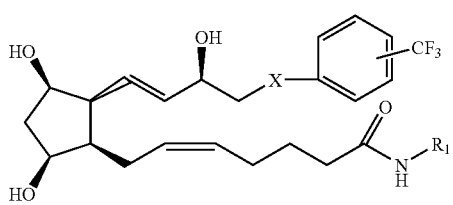

I in combination with a physiologically acceptable excipient, wherein X is O, S, or $CH_2$; and $R_1$ is methyl, ethyl, propyl or iso-propyl.

In a preferred embodiment, the compound is 7-(3,5-dihydroxy-2-(3-hydroxy-4-(3-(trifluoromethyl)phenoxy)-1-butenyl)cyclopentyl)-, N-ethyl, (1R-(1alpha(Z), 2beta(1E, 3R*), 3alpha, 5alpha), herein after referred to as "5-Heptenamide" having the structure of

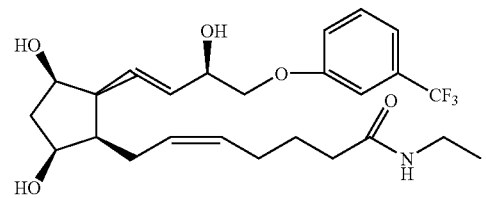

Optionally, the composition is formulated for topical application which can be in form of aqueous solution, emulsion, gel, lotion, ointment or cream. The composition may be used as a cosmetic, cosmeceutical, or pharmaceutical composition.

In another aspect, a topical cosmetic or cosmeceutical composition is provided. The composition comprises i) at least one Type-F prostaglandin analogue which is a 20-carbon unsaturated carboxylic acid, with two double bonds (cis at $C_5$; and trans at $C_{13}$) and a cyclopentane ring having hydroxy groups at $C_9$ and $C_{11}$ based on the structure of Type-F prostaglandin with the structure of

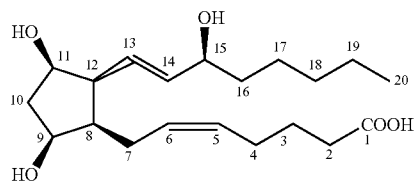

ii) at least one B-complex vitamin or derivative thereof, and
iii) optionally at least one mucopolysaccharide.

In a particular embodiment, the Type-F prostaglandin analogue is bimatoprost, also known as phenyl trinor $PGF_{2\alpha}$ amide, with the structure of

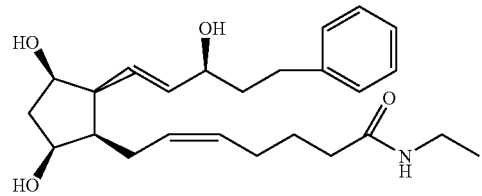

In other embodiments, the composition comprises a Type-F prostaglandin analogue such as bimatoprost.

The above composition may further comprise least one, preferably at least two, vitamins; at least one anti-inflammatory and/or antioxidant agent; or at least one 5-alpha-reductase inhibitor.

The composition of the present invention may be incorporated into mascara which may further optionally contain coloring agents.

Methods and kits are also provided for using the above compositions for conditioning, volumizing, extending, promoting growth of, and/or preventing loss of the hair such as hair on the scalp, eyelashes, eyebrows, mustache and beard of a mammal such as a human. Such compositions can be used for pharmaceutical, therapeutic, cosmeceutical or purely for cosmetic use. For example, the methods and composition of the present invention can be used to treat, prevent and/or reduce the risk of developing alopecia, male pattern baldness, autoimmune diseases, hair loss, miniaturization or thinning which may be due to pregnancy, hormone, chemotherapy, chemical treatment or other drug use, radiation, aging or other reasons. The methods and composition of the present invention can also be used for increasing hair pigmentation, restructuring and/or increase the volume of the hair shaft which are especially highly desirable for the aging population, and allows the delay of dying hair or reduce the frequency of dying hair, or eliminate the need for dying the hair.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

In FIGS. 1-12 described below, each subject was instructed to apply an embodiment of the inventive compositions once per day in the evening with an applicator brush in a thin line along upper lashes at the root area (as though she is applying eyeliner to her eyes).

In FIGS. 13-15 described below, each subject was instructed to shampoo and condition her hair as usual; apply once daily an embodiment of the inventive compositions as described in Example 7 (Hair-Conditioning Formulation A). by wetting hair on the scalp, spraying the composition very sparingly to the root area of the hair and messaging it over the entire scalp; and optionally apply leave-in conditioner (if normally used) or styling aids as usual and finishing styling hair.

DETAILED DESCRIPTION OF THE INVENTION

Figure 1B:
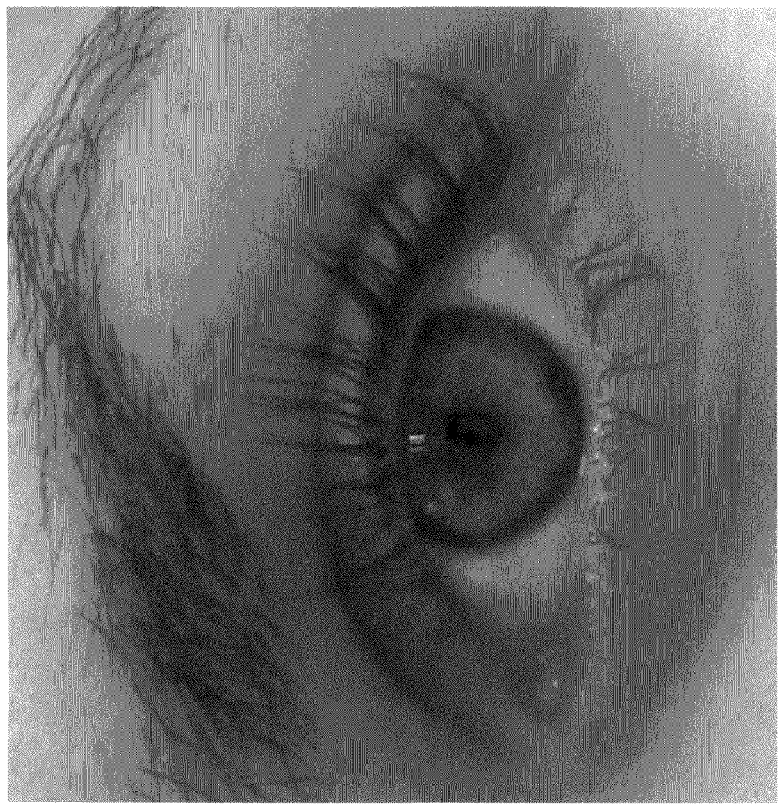
FIGS. 1A-F show the changes of eyelash appearance in a 22 year old female subject with topical application of an embodiment of the inventive compositions described in Example 1 (Lash-Conditioning Formulation A). Panel A: Before the application of the composition. Panel B: About 4 months after the application of the composition. Panel C: Same as Panel B. Panel D: About 6 months after the application of the composition. Panel E: Same as Panel F: Same as Panel D.
Figure 1A:
Figure 1D:
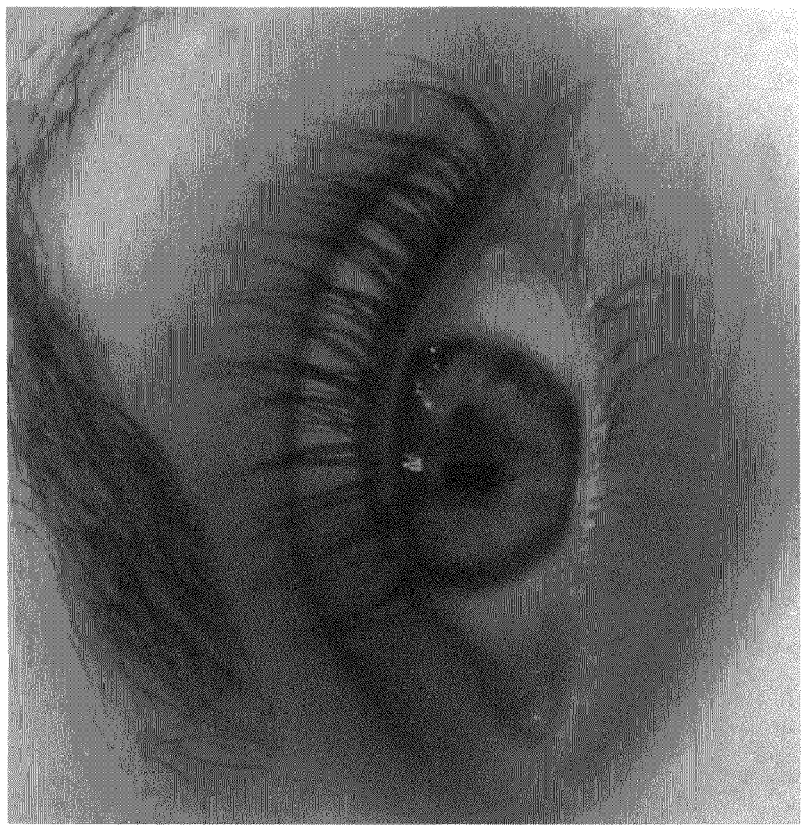
Figure 1C:
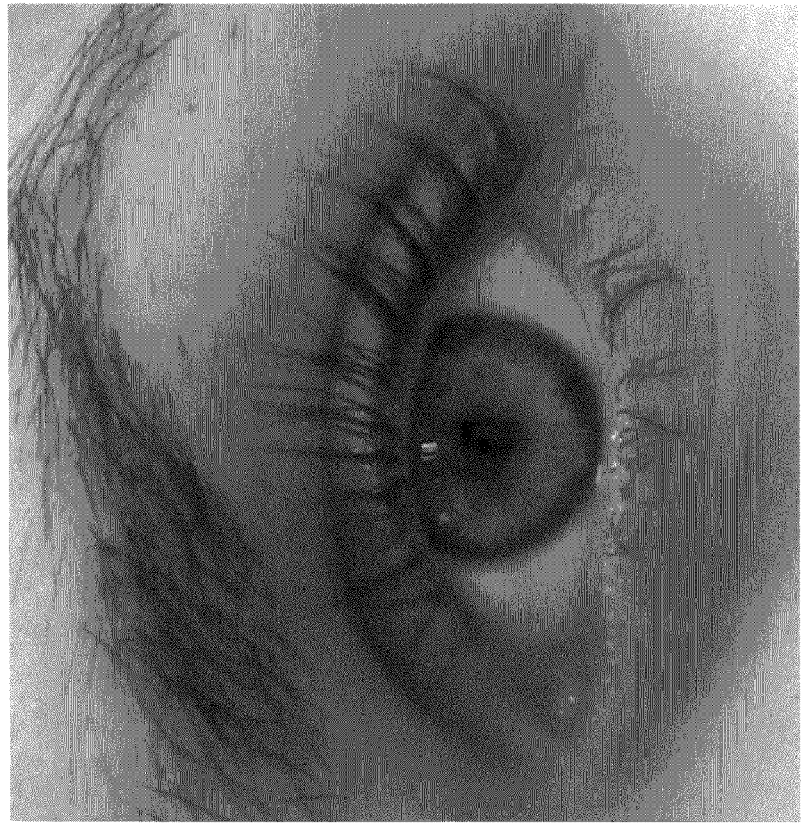
Figure 1F:
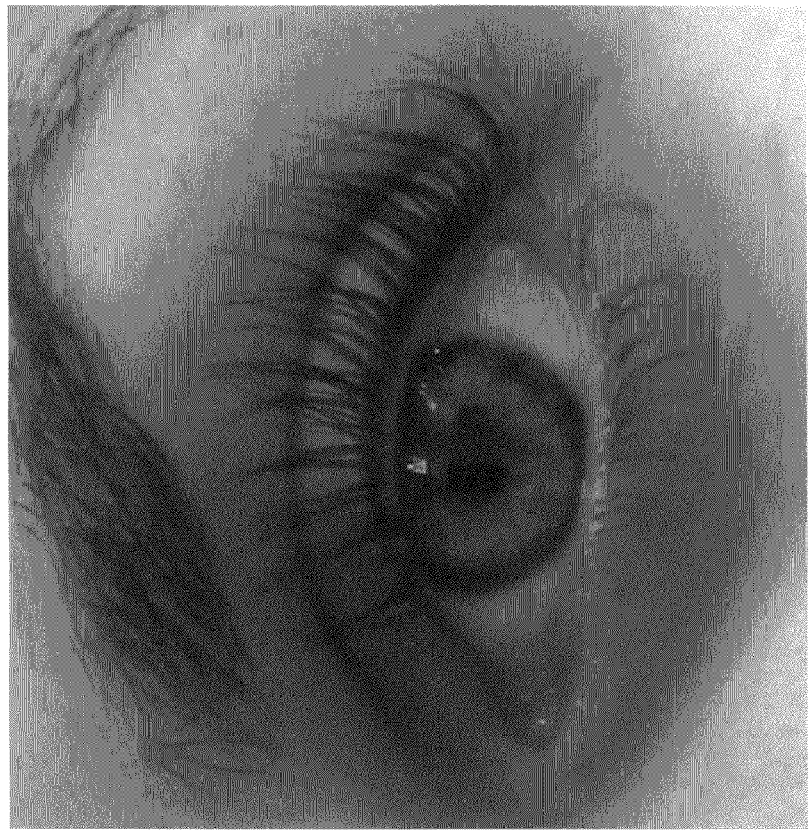
Figure 1E:
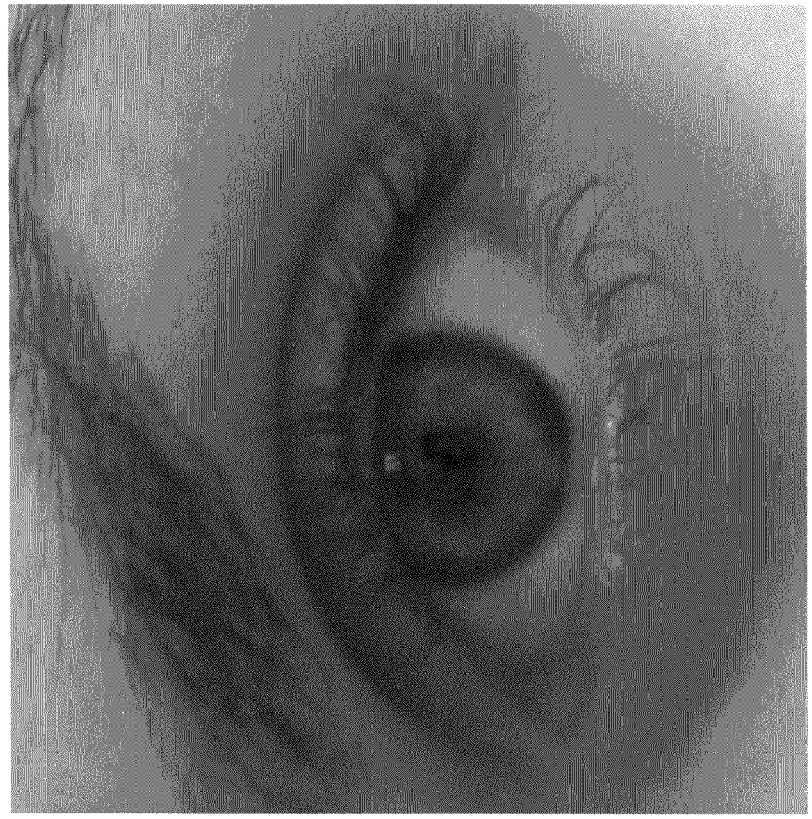

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention provides innovative compositions, kits and methods for conditioning and volumizing the hair, including but not limited to hair on the scalp, eyelashes, eyebrows, mustache and beard, promoting healthy growth and treating and preventing loss of hair.

In one aspect, a composition is provided, which can be useful for promoting hair growth, conditioning or preventing hair loss. The composition comprises compound of Formula I having the structure of

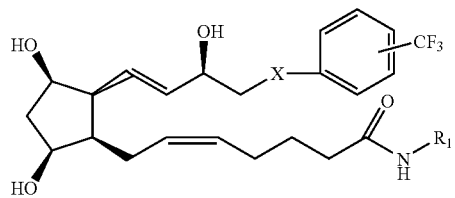

I in combination with a physiologically acceptable excipient, wherein X is O, S, or $CH_2$; and $R_1$ is methyl, ethyl, propyl or iso-propyl. The trifluoromethyl substituent may be at position 2, 3, 4, 5, or 6 of the benzene ring.

In a preferred embodiment, the compound is 7-(3,5-dihydroxy-2-(3-hydroxy-4-(3-(trifluoromethyl)phenoxy)-1-butenyl)cyclopentyl)-, N-ethyl, (1R-(1alpha(Z), 2beta(1E, 3R*), 3alpha, 5alpha), herein after referred to as "5-Heptenamide" having the structure of

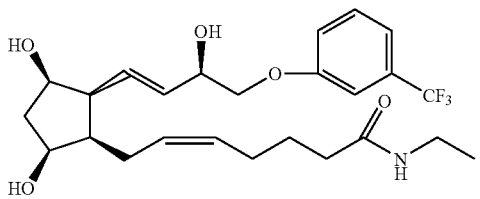

Optionally, the composition is formulated for topical application which can be in form of aqueous solution, emulsion, gel, lotion, ointment or cream. The composition may be used as a cosmetic, cosmeceutical, or pharmaceutical composition.

Prostaglandin analogues are derivatives of prostanoic acid. They are 20-carbon unsaturated carboxylic acids with a cyclopentane ring; they vary in number and position of double bonds, hydroxyl groups, and other substituents.

Prostaglandins are typically divided into types E, F, A, B, C and D. Of these, the first four are naturally-occurring; these have a trans-bond at the $C_{13}$ position, and a hydroxyl group at $C_{15}$. E- and F-type prostaglandins both have a hydroxyl substituent at $C_{11}$. Types E and F differ, however, at $C_9$. At that position, E-type prostaglandins have a carbonyl group, while F-type prostaglandins have a hydroxyl group.

In another aspect, a topical cosmetic or cosmeceutical composition is provided. The composition comprises i) at least one Type-F prostaglandin analogue which is a 20-carbon unsaturated carboxylic acid, with two double bonds (cis at $C_5$; and trans at $C_{13}$) and a cyclopentane ring having hydroxy groups at $C_9$ and $C_{11}$ based on the structure of Type-F prostaglandin with the structure of

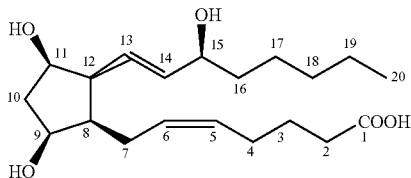

ii) at least one B-complex vitamin or derivative thereof, and
iii) optionally at least one mucopolysaccharide.

In a particular embodiment, the Type-F prostaglandin analogue is bimatoprost, also known as phenyl trinor $PGF_{2\alpha}$ amide, with the structure of

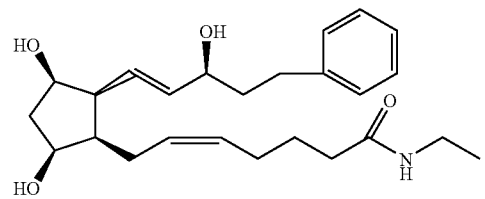

5-Heptenamide, 7-(3,5-dihydroxy-2-(3-hydroxy-4-(3-(trifluoromethyl)phenoxy)-1-butenyl)cyclopentyl)-, N-ethyl, (1R-(1alpha(Z), 2beta(1E,3R*), 3alpha, 5alpha) is also a Type-F prostaglandin analogue.

The inventor believes that the composition of the present invention especially the composition comprising the compound of Formula I has a proper balance of efficacy, bioavailability, safety and comfort for long term or daily use, whether or not it is used as a therapeutic, cosmetic or cosmeceutical.

In particular, the 5-Heptenamide administered to a mammal can be metabolized to produce an acid form which is a single isomer of fluprostenol, [+]fluprostenol having the structure of

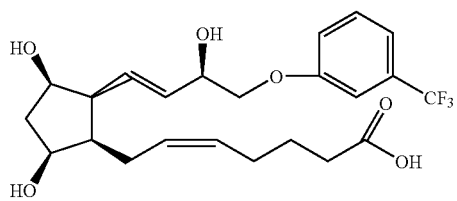

Since the compound of Formula I is an amide derivative of a $PGF_{2\alpha}$ analog, once absorbed, hydrolysis by enzymes in the body converts the amide back to the biologically active carboxylic acid. In particular, the 5-Heptenamide can be metabolized to [+]fluprostenol which then binds to the prostaglandin receptor with high affinity and has reduced side effects such as eye irritation and hyperemia (excess blood in vessels supplying the eye).

On the other hand, Travoprost, having a structure of

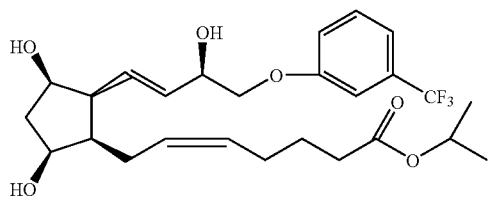

When absorbed in the body, is also metabolized into [+]fluprostenol. Based on extensive studies comparing the chemical structures, ocular and dermal absorption, metabolism, potency at the biological target site, toxicological and pharmacological of $PGF_{2\alpha}$ analogs and derivatives, such as bimatoprost and travoprost, the inventor believes that the compound of Formula I, in particular the 5-Heptenamide, has much more balanced and favorable profiles of safety and efficacy, especially for long term chronic application to the skin. It is assessed that compared with travoprost which is essentially completely converted [+]fluprostenol once absorbed in the body, the 5-Heptenamide is not as quantitatively converted to the acid form, similar to that of bimatoprost. Assuming an absorbed daily dosage of 0.020 μg/kg/day, due to tightness of the outmost keratinized skin layer (the stratum corneum) which causes percutaneous permeability of most drugs 100-1000 times less than through the conjunctiva (Urtti & Salminen (1993) Survey of Opthalmology 37:435-456) and the lower hydrolysis rate of the 5-Heptenamide than travoprost, the margin of safety for 5-Heptenamide is conservatively estimated to be about 71,000, which means normal use of the composition delivers a dose that is less than about one $71,000^{th}$ the no-observable-adverse-effect dose in long-term laboratory toxicity tests.

Traditionally, a margin of safety of 100 (10 for interspecies extrapolation, and 10 for inter species variability) is considered adequate. For reproductive effects, another 10-fold safety factor is usually applied, leading a margin of safety of 1000 to ensure public health protection. Thus, the composition of the present invention comprising the compound of formula, in particular, the 5-Heptenamide, has a safety margin far exceeding the required regulatory level, even for frequent, daily application to the skin.

As further demonstrated in the Example section, embodiments of the compositions of the present invention have been demonstrated to be highly efficacious in promoting lush hair growth, including growth of eyelashes and hair on the scalp, in humans, and in preventing hair loss, volumizing t the hair and enhancing hair pigmentation.

Preferably 5-Heptenamide is present at a concentration of from about 0.0001% to about 10%, from about 0.001% to about 5%, from about 0.005% to about 2%, from about 0.01% to about 0.5%, from about 0.0001% to about 10%, or about 0.02% to about 0.05% by weight of the total composition.

While not wishing to be bound to the theory, the inventor believes that the inventive composition can be used effectively to restructure or repair hair shaft, thereby volumizing the hair and preventing or inhibiting hair loss or miniaturization, perhaps through restoring the natural conformation of the hair proteins in the shaft by rearranging or rebuilding the disulfide bonds. The inventor also believes that additional ingredients in some embodiments of the inventive compositions, such as panthenol, hyaluronic acid, hyaluronate, glucosamine, glycosaminoglycan, 5-alpha reductase inhibitor such as spironolactone, Zinc PCA, biotin, and pantethine, may act synergistically to achieve desirable effects of the body hair as disclosed in the present invention.

In another embodiment, a second Type-F prostaglandin analogue—preferably, phenyl trinor $PGF_{2\alpha}$ amide (bimatoprost)—is present in addition to the 5-Heptenamide. Other Type-F prostaglandin analogues suitable for use in compositions of the present invention include those described in US Patent Application Publication Nos. 2003/0147823, 2004/0225014, 2004/0242665 and 2004/0052760. The disclosures of these references, including the teachings with respect to the concentration ranges and vehicles in which these Type-F prostaglandin analogues may be used are incorporated herein by reference.

Preferably, where phenyl trinor $PGF_{2\alpha}$ amide is present, it is at a concentration of from about 0.0001% to about 0.1% by weight of the total composition, more preferably from about 0.001% to about 0.05% by weight of the total composition. Optionally, phenyl trinor $PGF_{2\alpha}$ amide is at a concentration of from about 0.0001% to about 10%, from about 0.001% to about 5%, from about 0.005% to about 2%, from about 0.01% to about 0.5%, from about 0.0001% to about 10%, or about 0.02% to about 0.05% by weight of the total composition.

In a preferred embodiment, the at least one vitamin is a B-complex vitamin or a derivative, conjugate, homologue or analogue thereof and is selected from the group consisting of panthenol, pantothenic acid, pantetheine, pantethine, $C_1$-$C_{30}$ alkyl esters of pantothenic acid, $C_1$-$C_{30}$ carboxylic acid esters of panthenol, $C_1$-$C_{30}$ alkyl ethers of panthenol.

In a particularly preferred embodiment, the B-complex vitamin is pantethine, a dimer of Vitamin B5, in which two molecules of pantothenic acid are linked by cysteamine bridging groups. Preferably, pantethine is present at a concentration of from about 0.01% to about 1%, more preferably at least about 0.5%.

An even more preferred embodiment of the present invention is directed to a cosmetic composition comprising (i) the 5-Heptenamide of FIG. 1; (ii) a B-complex vitamin selected from the group consisting of panthenol, pantothenic acid, pantetheine, pantethine, $C_1$-$C_{30}$ alkyl esters of pantothenic acid, $C_1$-$C_{30}$ carboxylic acid esters of panthenol, $C_1$-$C_{30}$ alkyl ethers of panthenol; and (iii) retinol at a concentration of from about 0.01% to about 1.0%, preferably at a concentration of at least about 0.05%.

Antioxidant and/or anti-inflammatory agents suitable for use in the compositions of the present invention are well-known to those of ordinary skill in the art and include, but are not limited to: dipotassium glycyrrhetinate; allantoin; flavonoids, including green tea extract; enzymes, including superoxide dismutase, catalase and glutathione peroxidase; vitamins and vitamin derivatives, including ascorbic acid, tocopherol, and derivatives thereof. Additional antioxidant, radical scavengers and anti-inflammatory agents suitable for use in the compositions of the present invention may be in amount from about 0.1% to about 10%, more preferably from about 1% to about 5% by weight of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, lmethionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate.

In a preferred embodiment, the at least one antioxidant and/or anti-inflammatory agent is one or both of dipotassium glycyrrhetinate or green tea extract, each at a concentration of from about 0.01% to about 1.0%. Still more preferably, both dipotassium glycyrrhetinate and green tea extract are present.

In a preferred embodiment, the at least one 5-alpha-reductase inhibitor is spironolactone, preferably present at a concentration of from about 0.1% to about 30% by weight, from about 0.1% to about 12.5% by weight, or from about 1% to about 10% by weight, more preferably at a concentration of from about from about 2.5% to about 7.5% by weight of the total composition. The inventor realizes that solubilizing spironolactone has been a challenge and the traditional way of solubilizing spironolactone by using a concentrated alcohol solution (such as one containing 50-80% alcohol) is cosmetically undesirable as the high alcohol-content causes excessive drying and breakage of hair and loss of sheen and shine of the hair. According to the present invention, the composition preferably contains butylene glycol which not only solubilizes spironolactone but also circumvents the above-described problems associated with using high concentrated alcohol.

A more preferred embodiment of the present invention is directed to a composition comprising the 5-Heptenamide and at least two different alpha-reductase inhibitors such as spironolactone and Zinc PCA. Where the second alpha-reductase inhibitor is Zinc PCA, it is preferably present at a concentration of from about 0.01% to about 1.0%, more preferably at a concentration of at least about 0.1%, still more preferably at a concentration of at least about 0.2%.

Zinc PCA, available commercially under the trade name ZINCEDONE, is the zinc salt of L-Pyrrolidone Carboxylic Acid. Zinc PCA inhibits 5-alpha-reductase, helps regulates the activity of the sebaceous glands and reduces the level of skin sebum in vivo.

Panthenol (2,4-dihydroxy-N-(3-hydroxypropyl)-3,3-dimethylbutanamide), the reduced alcohol form of pantothenic acid (Vitamin $B_5$), is also preferably included in the compositions of the present invention. Panthenol in the composition can act as a humectant, emollient and/or moisturizer to nourish the skin and scalp. Preferably, panthenol (which can be in the D form as well as in a racemic mixture of D and L forms) is included in the compositions at concentrations of from about 0.1% to about 10%, or from 0.1% to about 1.0% by weight of the total composition.

Biotin, also known as Vitamin $B_7$, may be also included in the compositions of the present invention, preferably at concentrations of from about 0.001% to about 10%, from 0.001% to about 1.0%, or 0.005% to about 0.1% by weight of the total composition. Biotin can be used to further promote healthy growth of skin and hair.

Glycosamine and/or Glycosaminoglycans may be also included in the compositions of the present invention, preferably at concentrations of from about 0.1% to about 10%, from 0.1% to about 8%, 0.5% to about 7%, or 1% to about 5% by weight of the total composition. Glycosamine and/or Glycosaminoglycans with anti-inflammatory properties can be used to further promote healthy growth skin and hair.

Glycosaminoglycans, also known as mucopolysaccharides, are a family of unbranched polysaccharides consisting of two 6-carbon sugar derivatives—the first generically described as N-acetyl-D-hexosamine, the second a hexose or hexuronic acid. (Either or both of these sugar derivatives may be sulfated.) Members of the glycosaminoglycan family vary in terms of their hexosamine, hexose and hexuronic acid constituents and include glucuronic acid, iduronic acid, galactose, galactosamine and glucosamine.

Hyaluronic acid is a non-sulfated, disaccharide polymer comprised of alternating units of N-acetyl-D-glucosamine and D-glucuronic acid. In dermatocosmetic products, it is used both as an acid and as a sodium salt (i.e., sodium hyaluronate).

Preferably, the composition of the present invention further comprises glycosaminoglycans, biotin, hyaluronic acid and panthenol.

The compositions of the present invention may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. Preferred retinoids are retinol, retinyl palmitate, retinyl acetate, retinyl propionate, retinal and combinations thereof.

The compositions of the present invention may contain one or more of a thickening agent (thickener or gum), a humectant, a moisturizer, a hair conditioning agent and mixtures thereof.

Examples of the thickening agent include, but are not limited to, carboxylic acid polymers, cross-linked polyacrylate polymers, polyacrylamide polymers, polysaccharides and gums.

Carboxylic acid polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in CTFA International Cosmetic Ingredient Dictionary, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the CARBOPOL™ 900 series from B.F. Goodrich (e.g., CARBOPOL™ 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10}$-$C_{30}$ alkyl acrylate crosspolymers and are commercially available as CARBOPOL™1342, CARBOPOL™1382, PEMULEN TR-1, and PEMULEN TR-2, from B.F. Goodrich. In other words, examples of carboxylic acid polymer thickeners useful herein are those selected from carbomers, acrylates/$C_{10}$-$C_{30}$ alkyl acrylate crosspolymers, and mixtures thereof.

Crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

Polyacrylamide polymers, especially nonionic polyacrylamide polymers, include substituted branched or unbranched polymers. More preferred among these polyacrylamide polymers is the nonionic polymer given the CTFA designation polyacrylamide or isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides can be used as gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans which are a linear chain of (1-3) linked glucose units with a (1-6) linked glucose every three units, a commercially available example of which is CLEAROGEL™ CS11 from Michel Mercier Products Inc. (Mountainside, N.J.).

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Preferred compositions of the present invention include a thickening agent selected from carboxylic acid polymers, crosslinked polyacrylate polymers, polyacrylamide polymers, and mixtures thereof, more preferably selected from carboxylic acid polymers, polyacrylamide polymers, and mixtures thereof.

Compositions according to the present invention may be applied to the scalp or hair in any number of forms or vehicles known to those of skill in the art including as: (i) aqueous, aqueous-alcoholic or oily solutions, optionally gelled; (ii) an emulsion obtained by dispersing an aqueous phase in an oil or silicone phase, or vice versa (i.e., water-in-oil, oil-in-water, water-in-silicone, silicone-in-water); (iii) a triple emulsion, (i.e., water-in-oil-in-water or oil-in-water-in-oil); or (iv) a vesicular dispersion. The viscosity of the final formulation may be adjusted within the level of ordinary skill in the art to form a cream, lotion, gel, serum or spray.

In a preferred embodiment, a method is provided for conditioning scalp hair by applying to the scalp a conditioning composition comprising a compound having the structure of

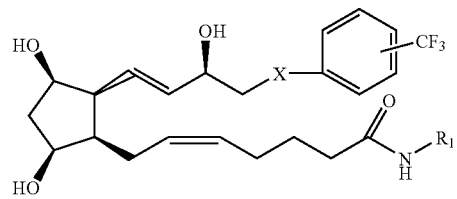

in combination with a physiologically acceptable excipient, wherein X is O, S, or $CH_2$; and $R_1$ is methyl, ethyl, propyl or iso-propyl.

Preferably, the compound is the 5-Heptenamide of the present invention, optionally in combination with at least one, B-complex vitamin derivative, at least one antioxidant and/or anti-inflammatory agent and at least one 5-alpha-reductase inhibitor, preferably spironolactone.

In another embodiment, a method is provided for promoting the growth and/or conditioning eyelashes by applying, at the lash line, a composition of the present invention which comprises a compound having the structure of

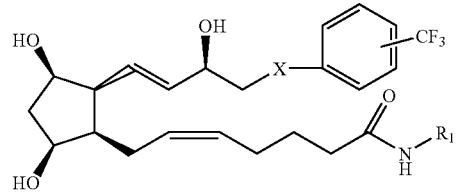

in combination with a physiologically acceptable excipient, wherein X is O, S, or $CH_2$; and $R_1$ is methyl, ethyl, propyl or iso-propyl.

Preferably the compound is the 5-Heptenamide of the present invention. Optionally, the composition further comprises at least one, preferably two, B-complex vitamins or their derivatives, and at least one mucopolysaccharide. In a preferred aspect of the present invention, the above-described compositions are applied at the lash line to create the appearance of thicker, longer and/or darker lashes.

In yet another embodiment, a method is provided for promoting the growth and/or conditioning eyelashes by applying, at the lash line, a composition of the present invention which comprises a Type-F prostaglandin analogue such as bimatoprost in combination with at least one B-complex vitamin; at least one anti-inflammatory and/or antioxidant agent; or at least one 5-alpha-reductase inhibitor. Preferably, the composition comprises bimatoprost, hyaluronic acid, panthenol and spironolactone, and more preferably further comprises glycosamine, glycosamineglycan, and/or a peptide such as Tri-, tetra-, penta-, hexa- and heptapeptides as well as oligopeptides (including palmitoyl and myristoyl derivatives thereof.

Preferably, the 5-Heptenamide is present at a concentration of from about 0.0001% to about 10%, from about 0.001% to about 5%, from about 0.005% to about 2%, from about 0.01% to about 0.5%, from about 0.0001% to about 10%, or about 0.02% to about 0.05% by weight of the total composition.

In another preferred aspect of the invention, the at least one B complex vitamin or B-complex vitamin derivative is a racemic mixture of D and L forms of panthenol. More preferably, DL Panthenol is present in a concentration of from about 0.1% to about 2.0% by weight of the total composition, more preferably from about 0.25% to about 1.0%.

In another more preferred embodiment of this aspect of the invention, the conditioning composition comprises the 5-Heptenamide and biotin. In this more preferred embodiment, biotin is present in a concentration of from about 0.0001% to about 0.15%, more preferably from about 0.001% to about 0.05% by weight of the composition.

In still another more preferred embodiment of this aspect of the invention, the at least one mucopolysaccharide is selected from the group consisting of hyaluronic acid and its salts, and hydrolyzed glycosaminoglycans. Preferably, the at least one mucopolysaccharide is sodium hyaluronate or hydrolyzed glycosaminoglycans.

In an even more preferred embodiment of this aspect of the present invention, the at least one mucopolysaccharide is sodium hyaluronate and hydrolyzed glycosaminoglycans and is present at a concentration of from about 0.05% to about 7% by weight of the composition. Preferably sodium hyaluronate and hydrolyzed glycosaminoglycans are present at a combined concentration of at least about 0.1% by weight of the composition, more preferably at a concentration of 1%.

A particularly preferred embodiment of this aspect of the present invention is directed to an eyelash conditioning composition comprising the 5-Heptenamide, a racemic mixture of D and L forms of panthenol and at least one mucopolysaccharide.

According to one aspect of this particularly preferred embodiment, the 5-Heptenamide of FIG. 1 is present at a concentration of from about 0.001% to about 0.05% by weight of the composition.

According to another aspect of this particularly preferred embodiment, the racemic mixture of D and L forms of panthenol is present at a concentration of from about 0.25% to about 1.0% by weight of the composition.

According to another aspect of this particularly preferred embodiment, the at least one mucopolysaccharide is present at a concentration of at least about 0.1% of the composition, preferably at least about 1%.

Optionally, the compositions of the present invention may also contain proteins, polypeptides (including acylated peptides), protein hydrolysates, derivatives and salts of proteins and polypeptides, as well as combinations thereof. Particularly preferred acylated peptides are comprised of (i) less than about ten amino acid residues, preferably less than about eight and (ii) a $C_{12}$-$C_{22}$ acyl group, preferably $C_{14}$-$C_{16}$.

Tri-, tetra-, penta-, hexa- and heptapeptides as well as oligopeptides (including palmitoyl and myristoyl derivatives thereof) suitable for incorporation in compositions of the present invention are commercially-available from a number of suppliers and are described in the *International Cosmetic Ingredient Dictionary and Handbook* (10th Edition, 2003) published by the Cosmetic, Toiletry and Fragrance Association ("INCI Dictionary"). These include acylated peptides further described in U.S. Pat. Nos. 6,974,799 and 6,492,326.

Optionally, the compositions of the present invention may contain spironolactone at a concentration of from about 0.01% to about 10.0% by weight of the total composition. In preferred embodiments of this aspect of the present invention, spironolactone is present at a concentration of at least about 0.1%, more preferably at a concentration of at least about 1% by weight of the composition.

The compositions of the present invention contain at least one rheological modifying agent, non-limiting examples of which include the following: Carbomer (a homopolymer of acrylic acid crosslinked with an allyl ether of pentaerythritol, an allyl ether of sucrose, or an allyl ether of propylene), acrylate/alkyl acrylate crosspolymers, xanthan gum, locust bean gum, guar gum, and any combination of any of the foregoing. A preferred rheological modifying agent is an acrylate/alkyl acrylate crosspolymer; preferably, the alkyl acrylates are $C_{10}$-$C_{30}$ alkyl acrylates.

The lash-conditioning compositions of the present invention may also contain humectants, moisturizers, hair conditioning agents, vitamins and derivatives thereof, and any combination of any of the foregoing. By "hair-conditioning agents" are meant ingredients which enhance the appearance and feel of hair, increase hair body and suppleness, facilitate styling, improve gloss and sheen and otherwise improve the texture of hair. Hair conditioning agents are well-known to those of skill in the art. Non-limiting examples of hair conditioning agents within the scope of the present invention are taught in the patent documents referenced hereinabove as well as in the following publications, all of which are incorporated herein by reference: *INCI Dictionary* (10th Ed.), pp. 2217-2227; U.S. Pat. No. 6,896,877 (including, without limitation, Column 16, line 57-Column 23, line 58); US Patent Application Publication No. 2005/0042191 (including, without limitation, "keratin conditioning agents" disclosed in Paragraphs 0033-0036.)

A particular aspect of the present invention is directed to conditioning the eyelashes by applying, at the lash line, a composition comprising the 5-Heptenamide in combination with at least one, preferably two, B-complex vitamins or their derivatives, and at least one mucopolysaccharide. By "lash line" is meant the point at which the eyelashes contact the eyelid margin. Preferred embodiments of this aspect of the invention include application of the particularly preferred compositions of the first aspect of the invention as described hereinabove.

In this aspect of the invention, the lash-conditioning composition is applied to the lashes using a wand, brush or similar bristled applicator of the type used to apply mascaras which are well-known to those of skill in the art.

Methods and kits are also provided for using the above compositions for conditioning, volumizing, extending, promoting growth of, and/or preventing loss of the hair, such as hair on the scalp, eyelashes, eyebrows, mustache and beard of a mammal such as a human. Such compositions can be used for pharmaceutical, therapeutic, cosmeceutical or purely for cosmetic use. For example, the methods and composition of the present invention can be used to treat, prevent and/or reduce the risk of developing alopecia, male pattern baldness, hair loss, miniaturization or thinning which may be due to pregnancy, hormone, chemotherapy or other drug use, radiation, aging or other reasons. The methods and composition of the present invention can also be used for increase hair pigmentation, restructuring and/or increase the volume of the hair shaft which are especially highly desirable for the aging population, and allows the delay of dying hair or reduce the frequency of dying hair, or eliminate the need for dying the hair.

In an aspect of the invention, a method is provided for promoting hair growth in a human subject by topically applying an effective amount of the inventive composition to the body of the subject, such as to the scalp and to the root area of the eyelashes, such that the hair is grown at least about 10%, 25%, 33%, 50%, 75%, 90%, 100%, 150%, or 200% longer than that before the initial application of the inventive composition; or such that the density of the hair is increased at least about 10%, 25%, 33%, 50%, 75%, 90%, 100%, 150%, or 200% compared to that before the initial application of the inventive composition, after a certain period of time. For example, the method may include the step of applying the composition to the subject per day at least 3 days a week, preferably for at least 5 days a week, more preferably 7 days a week.

In another aspect of the invention, a method is provided for preventing or inhibiting hair loss in a human subject by topically applying an effective amount of the inventive composition to the body of the subject, such as to the scalp, to the root area of the eyelashes, eyebrows, mustache and beard.

In yet another aspect of the invention, a method is provided for preventing or inhibiting hair miniaturization in a human subject by topically applying an effective amount of the inventive composition to the body of the subject, such as such as to the scalp, to the root area of the eyelashes, eyebrows, mustache and beard.

In still another aspect of the invention, a method is provided for treating alopecia in a human subject by topically applying an effective amount of the inventive composition to the body of the subject, such as to the scalp, to the root area of the eyelashes, eyebrows, mustache and beard.

In still another aspect of the invention, a method is provided for treating baldness in a human subject by topically applying an effective amount of the inventive composition to the body of the subject, such as to the scalp, to the root area of the eyelashes, eyebrows, mustache and beard.

In still another aspect of the invention, a method is provided for preventing or inhibiting hair miniaturization in a human subject by topically applying an effective amount of the inventive composition to the body of the subject, such as to the scalp, to the root area of the eyelashes, eyebrows, mustache and beard.

In still another aspect of the invention, a method is provided for restructuring and/or increasing the volume of the hair shaft in a human subject by topically applying an effective amount of the inventive composition to the body of the subject, such as to the scalp, to the root area of the eyelashes, eyebrows, mustache and beard, such that the volume of the hair shaft is increased at least about 10%, 25%, 33%, 50%, 75%, 90%, 100%, 150%, or 200% compared to that before the initial application of the inventive composition; or such that the cross-sectional diameter of the hair shaft is increased at least about 10%, 25%, 33%, 50%, 75%, 90%, 100%, 150%, or 200% compared to that before the initial application of the inventive composition, after a certain period of time. For example, the method may include the step of applying the composition to the subject per day at least 3 days a week, preferably for at least 5 days a week, more preferably 7 days a week.

In still another aspect of the invention, a method is provided for enhancing pigmentation of the hair in a human subject by topically applying an effective amount of the inventive composition to the body of the subject, such as to the scalp, to the root area of the eyelashes, eyebrows, mustache and beard, such that the pigmentation of the hair is increased at least about 10%, 25%, 33%, 50%, 75%, 90%, 100%, 150%, or 200% compared to that of the natural hair (i.e., without dyeing or artificial coloring) before the initial application of the inventive composition after a certain period of time. For example, the method may include the step of applying the composition to the subject per day at least 3 days a week, preferably for at least 5 days a week, more preferably 7 days a week.

EXAMPLES

The following examples are illustrative of the present invention. The components and specific ingredients are presented as being typical, and various modifications can be derived in view of the foregoing disclosure within the scope of the invention. All percentages, ratios and proportions are by weight.

Example 1

Lash-Conditioning Formulation A

| | | Example (% w/w) | Minimum (% w/w) | Maximum (% w/w) |
|---|---|---|---|---|
| Part A | D.I. Water | qs to 100 | qs to 100 | qs to 100 |
| | Acrylates/$C_{10}$-$C_{30}$ Alkyl Acrylates Crosspolymer | 0.80 | 0.20 | 1.80 |
| Part B | DL-Panthenol, 50% | 0.50 | 0.10 | 2.00 |
| | Biotin, USP | 0.01 | 0.0001 | 0.15 |
| | Sodium Hyaluronate (and) Hydrolyzed Glycosaminoglycans | 3.00 | 0.05 | 7.00 |
| | $C_{12}$-$C_{15}$ Alkyl Benzoate | 0.50 | 0.01 | 1.50 |
| Part C | Triethanolamine | 1.20 | 0.20 | 2.80 |
| | D.I. Water | 1.00 | 0.10 | 2.50 |
| Part D | Propylene Glycol (and) Diazolidinyl Urea (and) Methylparaben (and) Propylparaben | 1.00 | 0.10 | 1.50 |
| | 5-Heptenamide, 7-(3,5-dihydroxy-2-(3-hydroxy-4-(3-(trifluoromethyl) phenoxy)-1-butenyl) cyclopentyl)-, N-ethyl, (1R-(1alpha(Z), 2beta(1E,3R*), 3alpha, 5 alpha) | 0.03 | 0.0001 | 0.10 |
| | D.I. Water | 4.50 | 1.00 | 10.00 |
| Part E | Sodium Phosphate, Dibasic | 0.01 | 0.0001 | 0.50 |
| | D.I. Water | 1.00 | 0.01 | 3.00 |
| Part F | Sodium Chloride 25% (w/v) | 0.07 | 0.0001 | 0.20 |

Pre-disperse Acrylates/$C_{10}$-$C_{30}$ Alkyl Acrylates Crosspolymer in water.

Separately, pre-mix ingredients in Parts B, C, D and E. Add sequentially as follows: Part B to Part A; Part C to A/B; Part D to A/B/C; Part E to A/B/C/D; Part F to A/B/C/D/E.

Example 2

Volumizing Effect of Lash-Conditioning Formulation

The volumizing effect of the lash-conditioning product of Example 1 is demonstrated through image analysis as further described below.

Individual test lashes sold under the tradename Perm Allure™ (available from Consolidated Eyelash Co., Cleveland, Ohio) are secured to a holding device. More particularly, the secured lash is placed on a ground glass light table, with artificial daylight coming from beneath the lash. Baseline photographs of lashes are taken with Kodak Ektachrome Daylight Film (100 ASA) using a Nikon F4 SLR with a 55 mm Nikon f1.6 lens coupled to an Edmund Scientific 5× fixed focus loupe (Edmund Scientific, NJ).

Following the baseline photographs, each secured lash receives a single application of the lash-conditioning product of the present invention. By single application is meant two strokes applied by a trained technician, one to the top and one to the bottom of the lash. Each treated lash is allowed to dry and then photographed as described above. This is conducted on twenty-five separate lashes.

Pre- and post-treatment photographs are analyzed using an image analysis system that measures dimensional changes in the lashes. Photographic images are opened in the Image-Pro Plus software (Media Cybernetics, Silver Spring, Md.) and digitized by a high speed analog/digital converter with 8 byte resolution giving 256 levels of grey. Each scan line of the image is divided into pixels by a system clock which controls the sampling rate and scanning pattern within a 640×480 matrix.

Based on a grey-level slice technique, Image-Pro Plus software creates binary images of the lashes. Each lash is isolated as the only object in the measurement field. Area (the number of pixels within the boundary of the object) and perimeter (number of pixels along the boundary of the object) are measured. A quantitative assessment of the volumizing (i.e., thickening) effect of the conditioning treatment on the test lashes is manifested in terms of increased area of the lash.

In a second series of test lashes, a single application of mascara is made to the top and bottom of the test lash. This is allowed to dry and is followed by a single application of the lash-conditioning product, again to the top and bottom of the lash. Photographs are taken and images analyzed as described above.

Lashes treated with a lash-conditioning product of the present invention are more volumized and appear thicker in comparison to lashes first treated with mascara. Without wishing to be bound by a theory, applicant believes application of the conditioning product of the present invention at the lash line has a volumizing effect because the pores of the hairs at the lash line have not been blocked or coated by prior application of mascara.

Example 3

Topical Application of Lash-Conditioning Formulation A to Human Subjects

In this study, each subject was instructed to apply Lash-Conditioning Formulation A (containing ingredients listed in the table in Example 1 in the column labeled as "Example") once per day in the evening with an applicator brush in a thin line along upper lashes at the root area (as though she is applying eyeliner to her eyes).

FIGS. 1A-F show the changes of eyelash appearance in a 22 year old female subject with topical application of the formulation. As clearly shown in these figures, the subject's eyelashes had grown much lusher, longer and thicker after only a few months of application of the formulation.

Figure 2B:
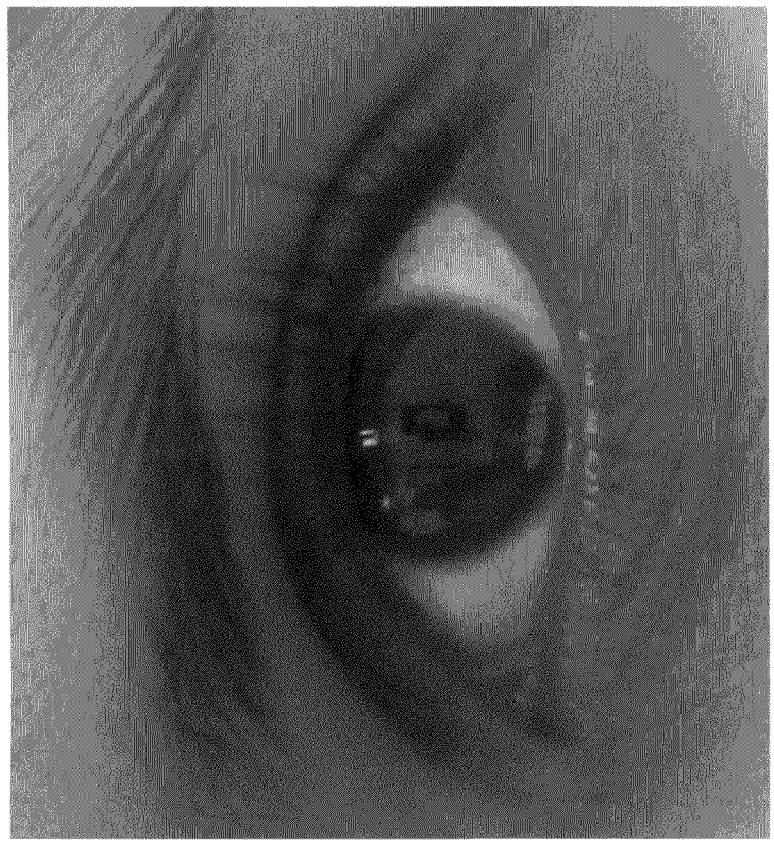
FIGS. 2A-B show the changes of eyelash appearance in a 32-year old female subject with topical application of an embodiment of the inventive compositions described in Example 1. Panel A: Before the application of the composition. Panel B: About 4 months after the application of the composition.
Figure 2A:
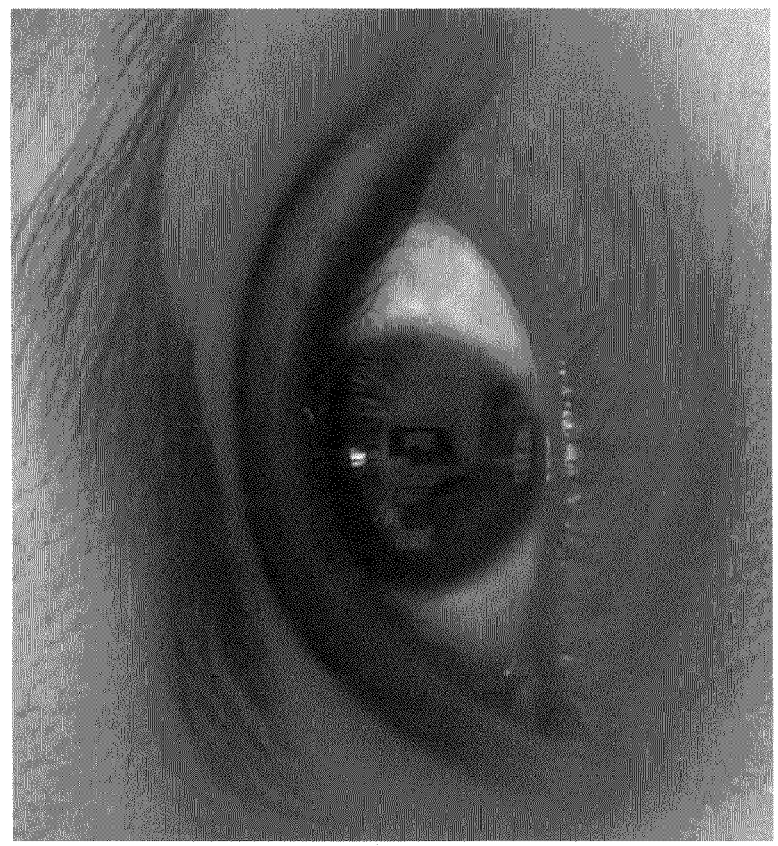

FIGS. 2A-B show the changes of eyelash appearance in a 32-year old female subject with topical application of the formulation. As clearly shown in these figures, the subject's eyelashes had grown much lusher, longer and thicker after about 4 months of application of the formulation.

Figure 3B:
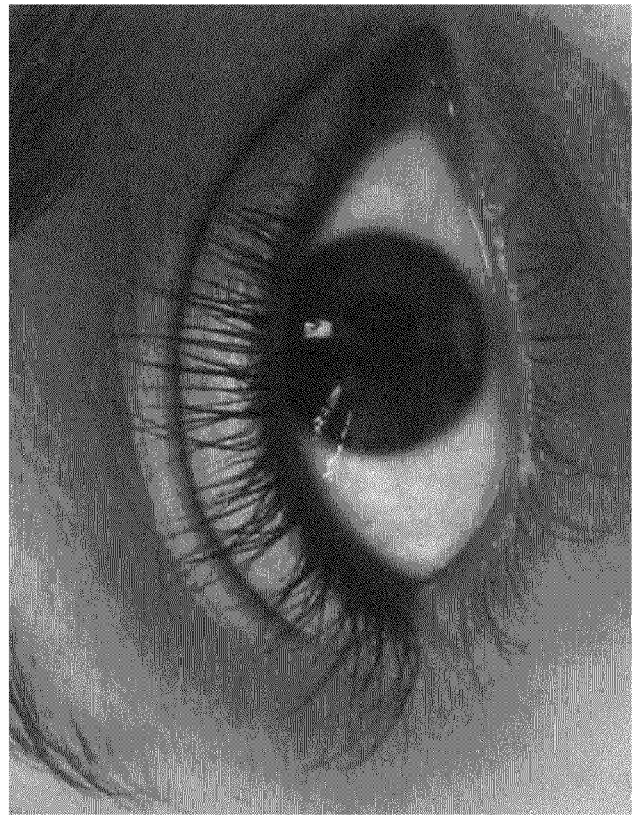
FIGS. 3A-B show the changes of eyelash appearance in a 21 year old female subject with topical application of Lash-Conditioning Formulation A. Panel A: Before the application of the composition. Panel B: About 11 months after the application of the composition.
Figure 3A:

FIGS. 3A-B show the changes of eyelash appearance in a 21 year old female subject with topical application of the formulation. As clearly shown in these figures, the subject's eyelashes had grown much lusher, longer and thicker after about 11 months of application of the composition.

Figure 4B:
FIGS. 4A-B show the changes of eyelash appearance in a 21 year old female subject with topical application of Lash-Conditioning Formulation A. Panel A: Before the application of the composition. Panel B: About 4 months after the application of the composition.
Figure 4A:

FIGS. 4A-B show the changes of eyelash appearance in a 21 year old female subject with topical application of the formulation. As clearly shown in these figures, the subject's eyelashes had grown much lusher, longer and thicker after about 4 months of application of the formulation.

Example 4

| | Lash-Conditioning Formulation B | |
|---|---|---|
| | | Concentration (% w/w) |
| Part A | D.I. Water | qs to 100 |
| | Acrylates/$C_{10}$-$C_{30}$ Alkyl Acrylates Crosspolymer | 0.80 |
| Part B | DL-Panthenol, 50% | 0.50 |
| | Biotin, USP | 0.01 |
| | Sodium Hyaluronate (and) Hydrolyzed Glycosaminoglycans | 3.00 |
| | $C_{12}$-$C_{15}$ Alkyl Benzoate | 0.50 |
| Part C | Triethanolamine | 1.20 |
| | D.I. Water | 1.00 |
| Part D | Propylene Glycol (and) Diazolidinyl Urea (and) Methylparaben (and) Propylparaben | 1.00 |
| | Phenyl trinor PGF2a amide | 0.03 |
| | D.I. Water | 4.50 |
| Part E | Sodium Phosphate, Dibasic | 0.01 |
| | D.I. Water | 1.00 |
| Part F | Sodium Chloride 25% (w/v) | 0.07 |

Pre-disperse Acrylates/$C_{10}$-$C_{30}$ Alkyl Acrylates Crosspolymer in water.

Separately, pre-mix ingredients in Parts B, C, D and E. Add sequentially as follows: Part B to Part A; Part C to A/B; Part D to A/B/C; Part E to A/B/C/D; Part F to A/B/C/D/E.

Example 5

Volumizing Effect of Lash-Conditioning Formulation

The volumizing effect of the lash-conditioning product of Example 4 is demonstrated through image analysis as further described below.

Individual test lashes sold under the tradename Perm Allure™ (available from Consolidated Eyelash Co., Cleveland, Ohio) are secured to a holding device. More particularly, the secured lash is placed on a ground glass light table, with artificial daylight coming from beneath the lash. Baseline photographs of lashes are taken with Kodak Ektachrome Daylight Film (100 ASA) using a Nikon F4 SLR with a 55 mm Nikon f1.6 lens coupled to an Edmund Scientific 5× fixed focus loupe (Edmund Scientific, NJ).

Following the baseline photographs, each secured lash receives a single application of the lash-conditioning product of the present invention. By single application is meant two strokes applied by a trained technician, one to the top and one to the bottom of the lash. Each treated lash is allowed to dry and then photographed as described above. This is conducted on twenty-five separate lashes.

Pre- and post-treatment photographs are analyzed using an image analysis system that measures dimensional changes in the lashes. Photographic images are opened in the Image-Pro Plus software (Media Cybernetics, Silver Spring, Md.) and digitized by a high speed analog/digital converter with 8 byte resolution giving 256 levels of grey. Each scan line of the image is divided into pixels by a system clock which controls the sampling rate and scanning pattern within a 640×480 matrix.

Based on a grey-level slice technique, Image-Pro Plus software creates binary images of the lashes. Each lash is isolated as the only object in the measurement field. Area (the number of pixels within the boundary of the object) and perimeter (number of pixels along the boundary of the object) are measured. A quantitative assessment of the volumizing (i.e., thickening) effect of the conditioning treatment on the test lashes is manifested in terms of increased area of the lash.

In a second series of test lashes, a single application of mascara is made to the top and bottom of the test lash. This is allowed to dry and is followed by a single application of the lash-conditioning product, again to the top and bottom of the lash. Photographs are taken and images analyzed as described above.

Lashes treated with a lash-conditioning product of the present invention are more volumized and appear thicker in comparison to lashes first treated with mascara. Without wishing to be bound by a theory, applicant believes application of the conditioning product of the present invention at the lash line has a volumizing effect because the pores of the hairs at the lash line have not been blocked or coated by prior application of mascara.

Example 6

Topical Application of Lash-Conditioning Formulation B to Human Subjects

In this study, each subject was instructed to apply Lash-Conditioning Formulation B once per day in the evening with an applicator brush in a thin line along upper lashes at the root area (as though she is applying eyeliner to her eyes).

Figure 5B:
FIGS. 5A-B show the changes of eyelash appearance in a 55 year old female subject with topical application of an embodiment of the inventive compositions described in Example 4 (Lash-Conditioning Formulation B). Panel A: Before the application of the composition. Panel B: About 7 months after the application of the composition.
Figure 5A:

FIGS. 5A-B show the changes of eyelash appearance in a 55 year old female subject with topical application of the formulation. As clearly shown in these figures, the subject's eyelashes had grown much lusher, longer and thicker after about 7 months of application of the formulation.

Figure 6B:
FIGS. 6A-B show the changes of eyelash appearance in a 33 year old female subject with topical application of Lash-Conditioning Formulation B. Panel A: Before the application of the composition. Panel B: About 6 months after the application of the composition.
Figure 6A:

FIGS. 6A-B show the changes of eyelash appearance in a 33 year old female subject with topical application of the formulation. As clearly shown in these figures, the subject's eyelashes had grown much lusher, longer and thicker after about 6 months of application of the formulation.

Figure 7B:
FIGS. 7A-B show the changes of eyelash appearance in a 32 year old female subject with topical application of Lash-Conditioning Formulation B. Panel A: Before the application of the composition. Panel B: About 6 months after the application of the composition.
Figure 7A:

FIGS. 7A-B show the changes of eyelash appearance in a 32 year old female subject with topical application of the formulation. As clearly shown in these figures, the subject's eyelashes had grown much lusher, longer and thicker after about 6 months of application of the formulation.

Figure 8B:
FIGS. 8A-B show the changes of eyelash appearance in a 28 year old female subject with topical application of Lash-Conditioning Formulation B. Panel A: Before the application of the composition. Panel B: About 3 months after the application of the composition.
Figure 8A:
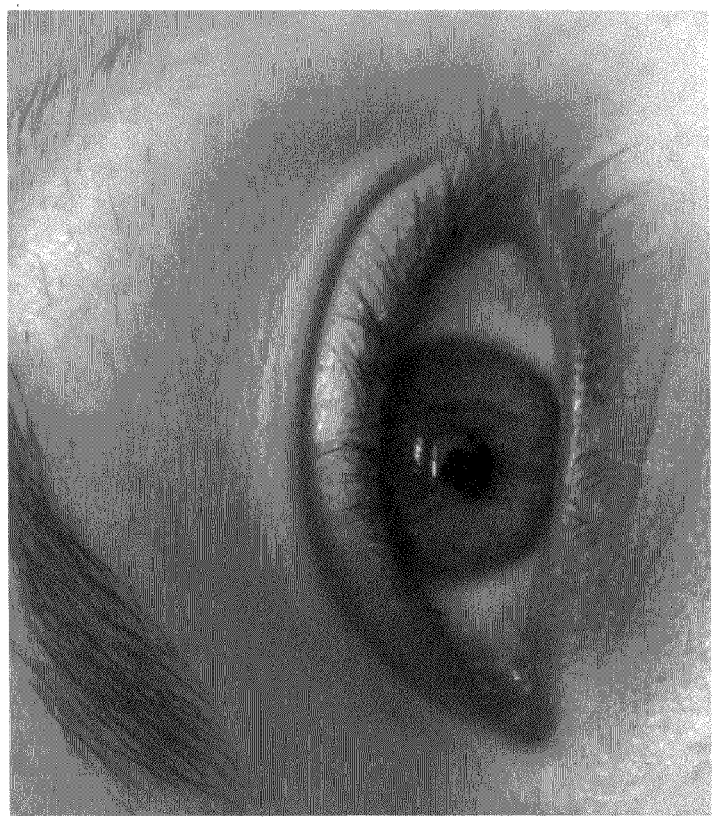

FIGS. 8A-B show the changes of eyelash appearance in a 28 year old female subject with topical application of the formulation. As clearly shown in these figures, the subject's eyelashes had grown much lusher, longer and thicker after about 3 months of application of the formulation.

Figure 9B:
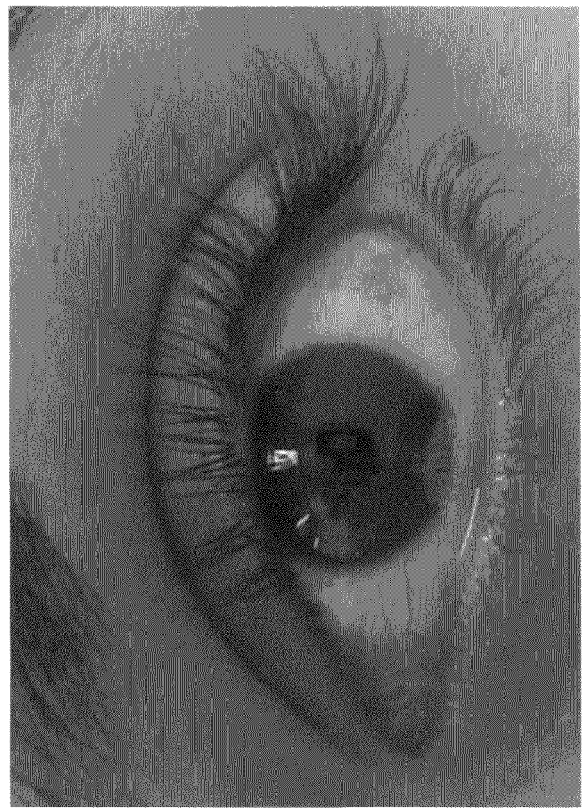
FIGS. 9A-B show the changes of eyelash appearance in a 21 year old female subject with topical application of Lash-Conditioning Formulation B. Panel A: Before the application of the composition. Panel B: About 5 months after the application of the composition.
Figure 9A:

FIGS. 9A-B show the changes of eyelash appearance in a 21 year old female subject with topical application of the formulation. As clearly shown in these figures, the subject's eyelashes had grown much lusher, longer and thicker after about 5 months of application of the formulation.

Figure 10B:
FIGS. 10A-B show the changes of eyelash appearance in a 21 year old female subject with topical application of Lash-Conditioning Formulation B. Panel A: Before the application of the composition. Panel B: About 4 months after the application of the composition.
Figure 10A:

FIGS. 10A-B show the changes of eyelash appearance in a 21 year old female subject with topical application of the formulation. As clearly shown in these figures, the subject's eyelashes had grown much lusher, longer and thicker after about 4 months of application of the formulation.

Figure 11B:
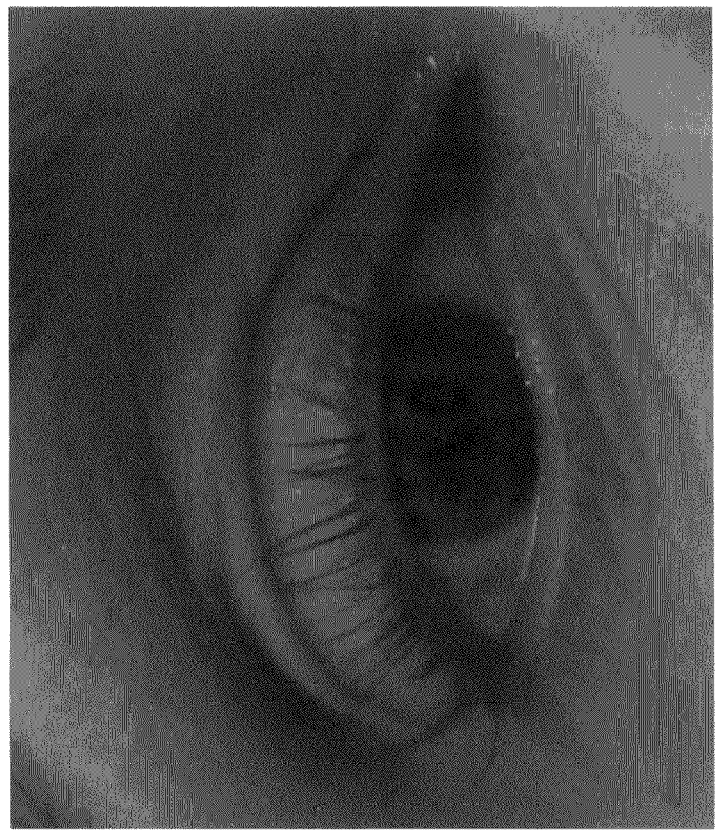
FIGS. 11A-B show the changes of eyelash appearance in a 45 year old female subject post chemotherapy with topical application of Lash-Conditioning Formulation B. Panel A: Before the application of the composition. Panel B: About 3 months after the application of the composition.
Figure 11A:

FIGS. 11A-B show the changes of eyelash appearance in a 45 year old female subject post chemotherapy with topical application of the formulation. As clearly shown in these figures, the subject's eyelashes had grown much lusher, longer and thicker after about 3 months of application of the formulation. These results also demonstrate that the inventive composition can promote lush, healthy hair growth even for a human whose has undergone chemotherapy which typically results in alopecia or hair thinning or loss.

Figure 12B:
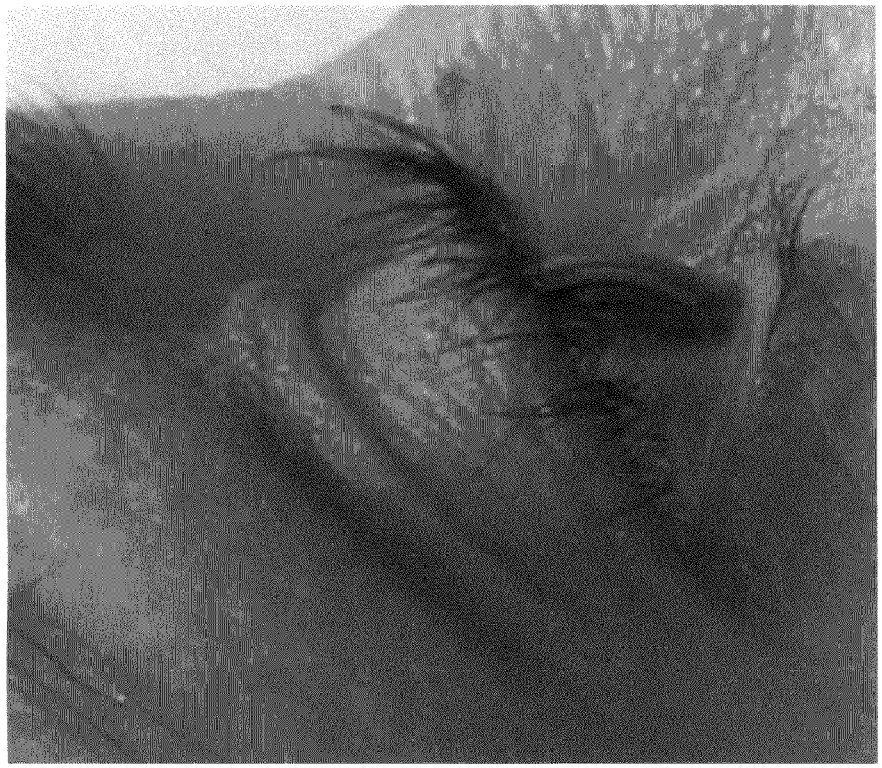
FIGS. 12A-B show the changes of eyelash appearance in a 47 year old female subject post chemotherapy with topical application of Lash-Conditioning Formulation B. Panel A: Before the application of the composition. Panel B: About 3 months after the application of the composition.
Figure 12A:

FIGS. 12A-B show the changes of eyelash appearance in a 47 year old female subject post chemotherapy with topical application of the formulation. As clearly shown in these figures, the subject's eyelashes had grown much lusher, longer and thicker after about 3 months of application of the formulation. These results again demonstrate that the inventive composition can promote lush, healthy hair growth even for a human whose has undergone chemotherapy which typically results in alopecia or hair thinning or loss.

Example 7

Hair-Conditioning Formulation A

The formulations listed below are illustrative of the present invention. Upper and lower ingredient ranges are also provided. The components and specific ingredients are presented as being typical, and various modifications, can be derived in view of the foregoing disclosure within the scope of the invention. All percentages, ratios and proportions are by weight.

| Ingredient | Example (% w/w) | Low (% w/w) | High (% w/w) |
|---|---|---|---|
| Part A | | | |
| 1  Deionized Water | 73.44 | QS to 100 | QS to 100 |

-continued

| Ingredient | Example (% w/w) | Low (% w/w) | High (% w/w) |
|---|---|---|---|
| 2 Dipotassium Glycyrrhetinate | 0.01 | 0.01 | 1.0 |
| 3 Niacinamide | 0.001 | 0.0001 | 0.1 |
| 4 Zinc PCA | 0.2 | 0.01 | 1.0 |
| Part B | | | |
| 5 Steareth-100 (and) Steareth-2 | 2.0 | 0.5 | 4.0 |
| 6 Hydroxypropyl Starch Phosphate Ester | 2.15 | 0.1 | 6.0 |
| Part C | | | |
| 7 Butylene Glycol | 15 | 5 | 25 |
| 8 Spironolactone | 5 | 0.1 | 12.5 |
| Part D | | | |
| 9 Propylene Glycol (and) Diazolidinyl Urea (and) Methylparaben (and) Propylparaben | 1.0 | 0.75 | 1.5 |
| 10 5-Heptenamide, 7-(3,5-dihydroxy-2-(3-hydroxy-4-(3-(trifluoromethyl)phenoxy)-1-butenyl)cyclopenty1)-, N-ethyl, (1R-(1alpha(Z),2beta(1E,3R*),3alpha,5alpha)) | 0.0005 | 0.0001 | 0.01 |
| Part E | | | |
| 11 Hydrolyzed Wheat Protein | 0.05 | 0.01 | 1.0 |
| 12 Japanese Green Tea Extract | 0.05 | 0.01 | 1.0 |
| 13 Retinol | 0.05 | 0.01 | 1.0 |
| 14 Pantethine | 0.5 | 0.01 | 1.0 |
| 15 Fragrance | 0.5 | 0.01 | 1.0 |
| 16 Hydrolyzed Oat Protein | 0.05 | 0.01 | 1.0 |

Dissolve Ingredients 2, 3 and 4 in Deionized Water. Premix Part B ingredients; add to Part A at 80-90° C. Premix. Part C ingredients; add to mixture of Parts A and B. At or below 45° C. add, sequentially, Part D, E and F ingredients with mixing.

Example 8

Topical Application of Hair-Conditioning Formulation to Human Subjects

In this study, each subject was instructed to shampoo and condition her hair as usual; apply once daily an embodiment of the inventive compositions as described in Example 7 (Hair-Conditioning Formulation A containing ingredients listed in the table in Example 7 in the column labeled as "Example") by wetting hair on the scalp, spraying the composition very sparingly to the root area of the hair and messaging it over the entire scalp; and optionally apply leave-in conditioner (if normally used) or styling aids as usual and finishing styling hair.

Figure 13A:
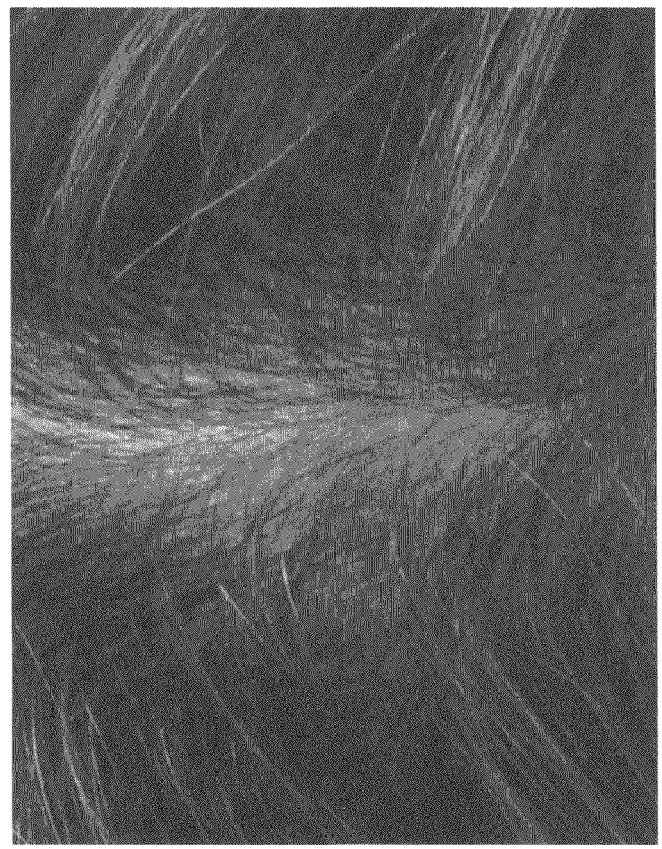
FIGS. 13A-B show the changes of hair appearance on the scalp of a 59 year old female subject with topical application of Hair-Conditioning Formulation A. Panel A: Before the application of the composition. Panel B: About 1.5 months after the application of the composition.
Figure 13B:
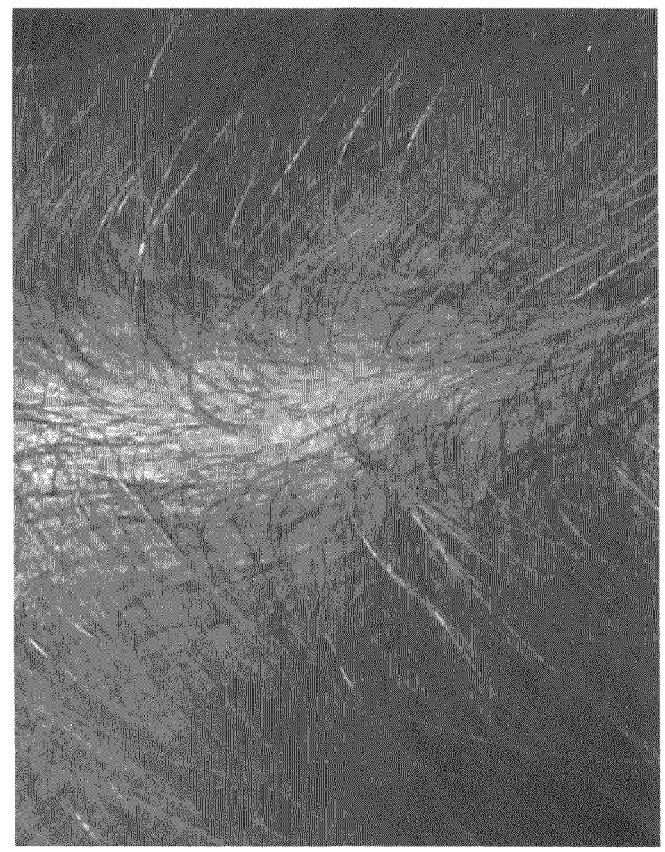

FIGS. 13A-B show the changes of hair appearance on the scalp of a 59 year old female subject with topical application of Hair-Conditioning Formulation A. As clearly shown these figures, the subject had grown thicker, denser hair with enhanced pigmentation on her scalp after about 1.5 months of application of the composition.

Figure 14B:
FIGS. 14A-B show the changes of hair appearance on the scalp of a 39 year old female subject with topical application of Hair-Conditioning Formulation A. Panel A: Before the application of the composition. Panel B: About 7 months after the application of the composition.
Figure 14A:
Figure 15B:
FIGS. 15A-H show the changes of hair appearance on the scalp of a 54 year old female subject with topical application of Hair-Conditioning Formulation A. Panel A: the hair on the top of the scalp before the application of the composition. Panel B: the hair on the top of the scalp about 4 months after the application of the composition. Panel C: the hair on the forehead before the application of the composition. Panel D: the hair on the forehead about 2 months after the application of the composition. Panel E: Same as panel D. Panel F: the hair on the forehead about 4 months after the application of the composition. Panel G: Same as Panel C. Panel H: Same as Panel F.
Figure 15A:
Figure 15D:
Figure 15C:
Figure 15F:
Figure 15E:
Figure 15H:
Figure 15G:
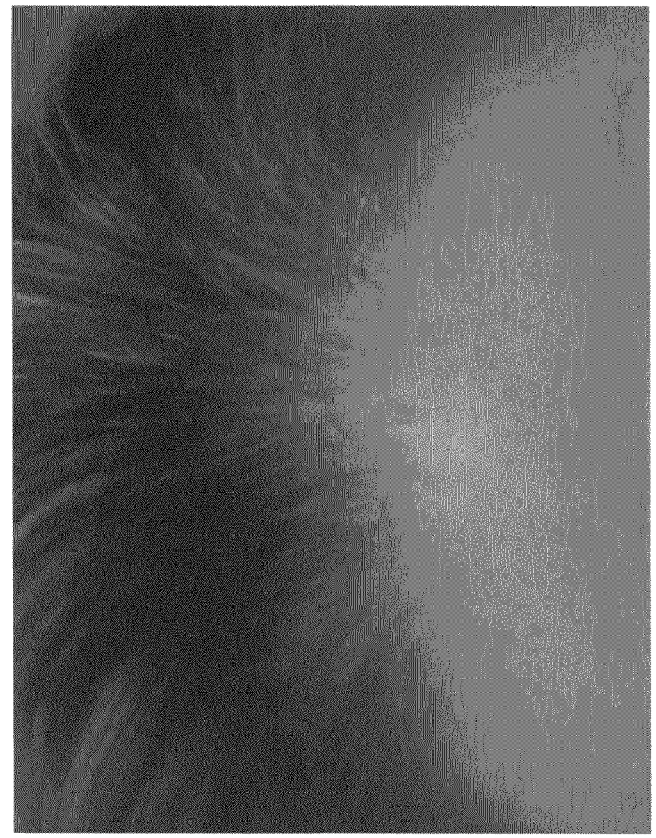

FIGS. 14A-B show the changes of hair appearance on the scalp of a 39 year old female subject with topical application of Hair-Conditioning Formulation A. As clearly shown these figures, the subject had grown thicker, denser hair with enhanced pigmentation on her scalp after about 7 months of application of the composition.

FIGS. 15A-H show the changes of hair appearance on the scalp of a 54 year old female subject with topical application of Hair-Conditioning Formulation A. As clearly shown these figures, the subject had grown thicker, denser hair with enhanced pigmentation on her scalp and filling in the once receding frontal hairline after about 4 months of application of the composition.

What is claimed is:

1. A composition comprising 7-(3,5-dihydroxy-2-(3-hydroxy-4-(3-(trifluoromethyl)phenoxy)-1-butenyl)cyclopentyl)-, N-ethyl, (1R-(1alpha(Z), 2beta(1E,3R*), 3alpha, 5alpha) (5-Heptenamide) having the structure of

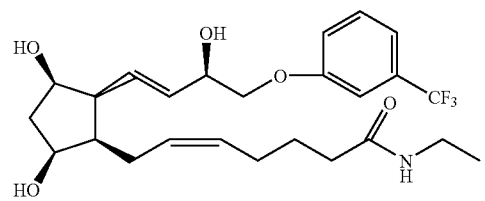

2. The composition of claim 1, wherein the composition is formulated for topical application.

3. The composition of claim 2, wherein the composition is in a form of aqueous solution, emulsion, gel, lotion, or cream.

4. The composition of claim 1, wherein the excipient is a cosmetically acceptable excipient.

5. The composition of claim 1, wherein the excipient is a pharmaceutically acceptable excipient.

6. The composition of claim 1, further comprising: one or more B-complex vitamin.

7. The composition of claim 1, further comprising: panthenol or pantethine.

8. The composition of claim 1, further comprising: a 5-alpha-reductase inhibitor.

9. The composition of claim 8, wherein the 5-alpha-reductase inhibitor is spironolactone or Zinc PCA.

10. The composition of claim 1, further comprising: hyaluronic acid or hyaluronate salt.

11. The composition of claim 1, further comprising: biotin.

12. The composition of claim 1, further comprising: glucosamine or glycosamineglycan.

13. The composition of claim 1, further comprising: a peptide or an acylated peptide.

14. The composition of claim 13, wherein the peptide is a cosmetically acceptable tri-, tetra-, penta-, hexa-, or heptapeptide or an acylated peptide thereof.

15. The composition of claim 1, further comprising: hyaluronic acid, panthenol, panthetine, spironolactone, peptide, and glucosamine or glycosamineglycan.

16. The composition of claim 1, wherein the concentration of compound of Formula I is about 0.001-0.5% by weight of the total composition.

17. The composition of claim 1, wherein the compound of Formula I is 5-Heptenamide at a concentration of about 0.01-0.1% by weight of the total composition.

18. A topical cosmetic or cosmeceutical composition, comprising:
   i) at least one Type-F prostaglandin analogue which is a 20-carbon unsaturated carboxylic acid, with two double bonds cis at $C_5$ and trans at $C_{13}$ and a cyclopentane ring having hydroxy groups at $C_9$ and $C_{11}$ based on the structure of Type-F prostaglandin with the structure of

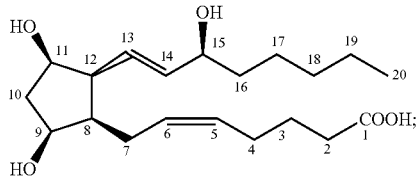

and
ii) at least one B-complex vitamin, and iii) at least one mucopolysaccharide.

19. The composition of claim 18, wherein the Type-F prostaglandin analogue is bimatoprost, with the structure of

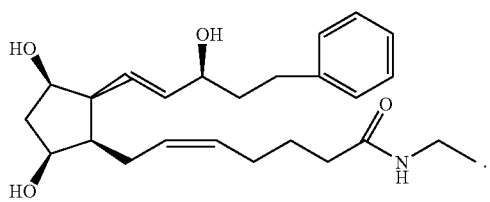

20. The composition of claim 18, wherein the B-complex vitamin is panthenol or pantethine.

21. The composition of claim 18, further comprising: a 5-alpha-reductase inhibitor.

22. The composition of claim 21, wherein the 5-alpha-reductase inhibitor is spironolactone or Zinc PCA.

23. The composition of claim 18, further comprising: glucosamine.

24. The composition of claim 18, further comprising: biotin.

25. The composition of claim 18, wherein the mucopolysaccharide is hyaluronic acid, hyaluronate salt or glycosamineglycan.

26. The composition of claim 18, further comprising: a peptide or an acylated peptide.

27. The composition of claim 26, wherein the peptide is a cosmetically acceptable tri-, tetra-, penta-, hexa-, or heptapeptide or an acylated peptide thereof.

28. The composition of claim 18, further comprising: hyaluronic acid, panthenol, panthetine, spironolactone, peptide, and glucosamine or glycosamineglycan.

29. The composition of claim 18, wherein the concentration of the Type-F prostaglandin analogue is about 0.001-0.5% by weight of the total composition.

30. The composition of claim 1, wherein the Type-F prostaglandin analogue is bimatoprost at a concentration of about 0.01-0.1% by weight of the total composition.

31. A method for promoting hair growth in a human subject, comprising topically applying an effective amount of: the composition of claim 1 or 18 to the body of the subject such that the length of the hair is grown at least about 10% longer than that before the initial application of the inventive composition.

32. The method of claim 31, wherein the hair is hair on the scalp, eyelashes, eyebrows, mustache or beard of the subject.

33. The method of claim 31, wherein the hair is grown at least about 50% longer than that before the initial application of the inventive composition.

34. The method of claim 31, wherein the density of the hair is increased at least about 10% than that before the initial application of the inventive composition.

35. The method of claim 31, wherein the composition is applied to the subject per day at least 3 days a week.

36. The method of claim 31, wherein the composition is applied to the root area of the eyelashes of the subject.

37. The method of claim 31, wherein the composition is applied to the scalp of the subject.

38. A method for inhibiting hair loss in a human subject, comprising: topically applying an effective amount of the composition of claim 1 or 18 to the body of the subject.

39. The method of claim 38, wherein the hair is hair on the scalp, eyelashes, eyebrows, mustache or beard of the subject.

40. A method for inhibiting hair miniaturization in a human subject, comprising: topically applying an effective amount of the composition of claim 1 or 18 to the body of the subject.

41. The method of claim 40, wherein the hair is hair on the scalp, eyelashes, eyebrows, mustache or beard of the subject.

42. A method for treating alopecia or baldness in a human subject, comprising: topically applying an effective amount of: the composition of claim 1 or 18 to the body of the subject.

43. The method of claim 42, wherein the composition is applied to the scalp, the root area of the eyelashes, eyebrows, mustache or beard of the subject.

44. The method of claim 42, wherein the alopecia or baldness is due to aging, chemotherapy, hormone, or environmental reasons.

45. A method for restructuring and/or increasing the volume of the hair shaft in a human subject, comprising: topically applying an effective amount of: the composition of claim 1 or 18 to the body of the subject, such that the volume of the hair shaft is increased at least about 10% compared to that before the initial application of the inventive composition.

46. The method of claim 45, wherein the cross-sectional diameter of the hair shaft is increased at least about 10% compared to that before the initial application of the inventive composition.

47. The method of claim 45, wherein the hair is hair on the scalp, eyelashes, eyebrows, mustache or beard of the subject.

48. The method of claim 45, wherein the composition is applied to the subject per day at least 3 days a week.

49. A method for enhancing pigmentation of the hair in a human subject, comprising: topically applying an effective amount of the composition of claim 1 or 18 to the body of the subject such that the pigmentation of the hair is increased at least about 10% compared to that of the natural hair of the subject.

50. The method of claim 49, wherein the hair is hair on the scalp, eyelashes, eyebrows, mustache or beard of the subject.

51. A kit, comprising: a vessel containing the composition of claim 1 or 18.

52. The kit of claim 51, further comprising: a printed instruction for how to use the composition.

53. The kit of claim 52, wherein the instruction includes instruction for how to topically apply the composition to the body of a human subject.

54. The kit of claim 53, wherein the instruction for how to topically apply the composition to the body of a human subject includes instruction for how to apply to the scalp, the root area of the eyelashes, eyebrows, mustache or beard of the subject.

55. The kit of claim 51, further comprising: an applicator for applying the composition to a human body.

56. The kit of claim 51, wherein the vessel contains mascara which includes the composition.

57. A method for manufacturing a topical composition, comprising:
dissolving a compound having the structure

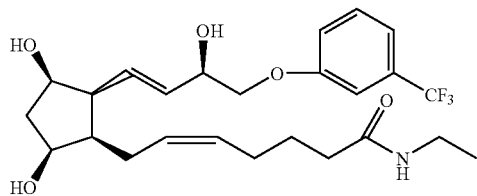

in propylene glycol; and mixing the solution of the compound with at least one physiologically acceptable excipient.

58. The method of claim 57, further comprising dissolving spironolactone in butylene glycol; and mixing the solution of spironolactone with the solution of the compound.

59. The method of claim 57, further comprising mixing the solution of the compound with hyaluronic acid, panthenol, panthetine, spironolactone, peptide, glucosamine or glycosamineglycan.

* * * * *